United States Patent [19]
Martin et al.

[11] Patent Number: 5,115,677
[45] Date of Patent: May 26, 1992

[54] METHODS AND DEVICES FOR DETERMINING THE CONTACT ANGLE OF A DROP OF LIQUID PLACED ON A SUBSTRATE

[75] Inventors: Philippe Martin, Fresnes; Gilles Le Boudec, Mareil Marly, both of France

[73] Assignee: Photonetics, Marly-le Roi, France

[21] Appl. No.: 504,799

[22] Filed: Apr. 5, 1990

[30] Foreign Application Priority Data

Apr. 6, 1989 [FR] France ............... 89 04530

[51] Int. Cl.⁵ .............................. G01N 13/02
[52] U.S. Cl. .................................... 73/64.48
[58] Field of Search .................. 73/64.4; 358/107

[56] References Cited
FOREIGN PATENT DOCUMENTS 0199312 10/1986 European Pat. Off. .
2574180 6/1986 France .
57-76439 5/1982 Japan .
60-85353 5/1985 Japan .

*Primary Examiner*—Jerry W. Myracle
*Attorney, Agent, or Firm*—Fleit, Jacobson, Cohn, Price, Holman & Stern

[57] ABSTRACT

The invention relates to improvements to methods and devices for determining the contact angle of a drop of liquid placed on a substrate. The device comprises: a support 12 for a substrate 11 which receives a drop of liquid 9; a light source 1; optical means, formed for example by a plate with parallel faces 21 rotatable about its axis 22 and whose inclination with respect to the axis may be modified, with a reflecting prism 5a, for forming a primary beam 6a, advantageously annular, striking the interface 8 between drop and substrate; a receiving surface 13a, 13b formed by a reflection diffusing surface; a reflecting surface 17; and a camera C.

7 Claims, 3 Drawing Sheets

METHODS AND DEVICES FOR DETERMINING THE CONTACT ANGLE OF A DROP OF LIQUID PLACED ON A SUBSTRATE

The present invention relates to the measurement of the contact angle of a drop of liquid placed on a horizontally disposed solid or liquid substrate.

From the value of the contact angle between a drop of liquid and the horizontal surface of a substrate which carries the drop certain properties of the substrate can be derived, particularly its wettability and its surface condition, properties which are useful in fundamental or applied research.

The French patent 2 574 180 of the Centre National de la Recherche Scientifique, which recalls the main applications of contact angle measurement, describes a method and device for determining the contact angle of a drop of liquid placed on a horizontal solid or liquid substrate, in which:

a primary beam of parallel light is directed perpendicularly to the substrate for illuminating a zone of the assembly formed by the drop of liquid and the horizontal substrate (which zone includes the interface between the periphery of the drop and the substrate) while producing a secondary beam by interaction with the drop and the substrate, and the extent of the illumination transition presented by the secondary beam in correspondence with the periphery of the drop is measured on a receiving surface intercepting this secondary beam.

However, the method and device of the above patent, which generally gives satisfactory results in the case of visual observation of the receiving surface, which is then a frosted surface, do not allow precise measurements to be made for all the drop-substrate pairs in the case of using a camera for displaying the illumination transition, in particular when the contact angle between the drop and the surface of the substrate is relatively high, for example close to 45°, and/or when the substrate is very diffusing.

In fact, although in the case, illustrated in FIG. 1, of a low contact angle, it is possible with a device of the type described in the above patent 2 574 180, to replace visual examination by a photographic image taken by a camera C, it is no longer the same in the case, illustrated in FIG. 2, of a contact angle close to 45°, for the following reason.

FIGS. 1 and 2 reproduce substantially FIG. 8 of the above patent, but simplifying it.

In these FIGS. 1 and 2, there have been designated:

by 1 a laser emitting a beam 2 of horizontal and parallel rays, by 3 an afocal optical system widening beam 2 into a more extensive beam 4, but also formed of horizontal and parallel rays, this afocal optical system being shown solely in FIG. 1 which illustrates a plano-concave lens 3a and a plano-convex lens 3b, by 5 a reflecting mirror, slanted by 45° with respect to the vertical, which produces the primary beam 6 of parallel light, vertical in direction, which illuminates on the assembly to be observed a zone 7 which includes the interface between the periphery 8 of drop 9 and the horizontal surface 10 of substrate 11, which is for example solid, carried movably by a sample-holder 12, and by 13 a receiving surface intercepting the secondary beam 14 resulting from the interaction of the primary beam with the drop 9 and substrate 11.

In FIGS. 1 and 2 have been shown, specially in the primary 6 and secondary 14 beams, the rays directed to and coming from the periphery 8 of drop 9, namely from the drop-substrate interface, the angle of these rays 14 of the secondary beam with respect to the vertical, so with the corresponding rays 6 of the primary beam, being twice ($2\theta$) the drop-substrate contact angle referenced $\theta$.

Although a camera C may, in the case of FIG. 1 where the contact angle $\theta$ is relatively small (for example not exceeding 10° to 20°), receive a large part of the rays such as 15 from the receiving surface 13 and corresponding to the rays 14 of the secondary beam from the periphery 8 of drop 9, it is no longer the same in the case of FIG. 2, where the contact angle $\theta'$ is relatively close to 45°, for example about 40° and so the angle $2\theta'$ about 80°, for then camera C receives practically no rays 15' from the receiving surface 13 and corresponding to the rays of the secondary beam 14 from the periphery 8 of drop 9.

Consequently, although the illumination transition corresponding to the periphery 8 of drop 9 can be readily detected by camera C in FIG. 1 which receives numerous rays from surface 13, on the other hand observation of this transition is difficult using camera C of FIG. 2 which receives very few rays from this surface 13.

In order to observe the illumination transition corresponding to the periphery of the drop under excellent conditions, using a camera, even for a relatively high contact angle which may reach about 45°, in accordance with the invention, the surface receiving the secondary beam is formed by a reflection diffusing surface and a reflecting surface is disposed for reflecting the light from this receiving surface towards the camera, so as to concentrate on the objective of the latter at least the majority of rays forming the secondary beam and corresponding particularly to the periphery of the drop.

The object of the invention is first of all to provide a method for determining the contact angle of a drop of liquid placed on a substrate, for any contact angle less than 45°, which consists in directing perpendicularly to the substrate a primary beam of parallel light for illuminating a zone which contains the interface between the periphery of the drop and the substrate, determining the illumination transition zone presented by a secondary beam resulting from the interaction of the primary beam with the drop and the substrate, on at least one receiving surface intercepting this beam, and is characterized in that said receiving surface is a reflection diffusing surface, in that a reflecting surface is provided disposed inside said diffusing receiving surface for reflecting the light rays from said diffusing receiving surface, and in that the rays reflected by said reflecting surface are collected by a camera.

The invention also has as object a device for implementing the above method, comprising a support for holding a substrate horizontal on which is placed a drop of liquid, a light source associated with optical means for forming from the light source a primary beam of parallel light directed perpendicularly to the substrate, at least one receiving surface surrounding the substrate for intercepting the returning secondary beam produced by interaction of the primary beam with the drop and the substrate, and is characterized in that said receiving surface is formed by a reflection diffusing surface, in that a reflecting surface is disposed inside said diffusing receiving surface for reflecting the beam of rays reflected by said diffusing receiving surface and in that it comprises a camera disposed for collecting the rays reflected by said reflecting surface.

The invention will in any case be well understood from the following complement of description and the accompanying drawings, which complement and drawings are of course given by way of example.

FIGS. 1 and 2, already described above, illustrate schematically the problems arising from the use of a device according to FIG. 8 of the above mentioned French patent when it is desired to use a camera for observing the surface receiving the secondary beam, respectively in the case of a relatively small contact angle and a relatively high contact angle.

Figure 3:
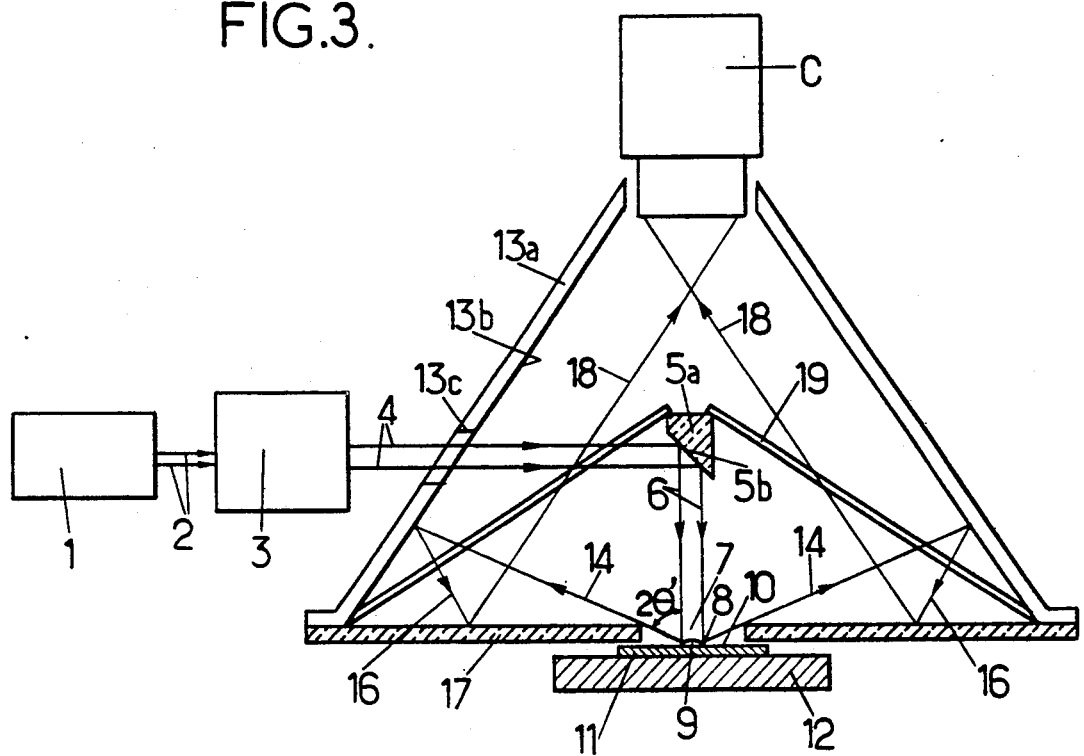
FIG. 3 illustrates one embodiment of a device comprising the improvements according to the invention.
Figure 6:
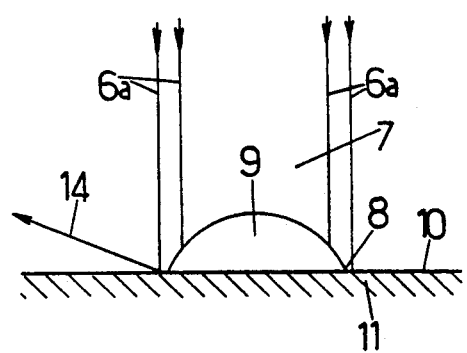
FIG. 6 shows schematically how this disadvantage may be avoided using an accessory characteristic of the invention.
Figure 7:
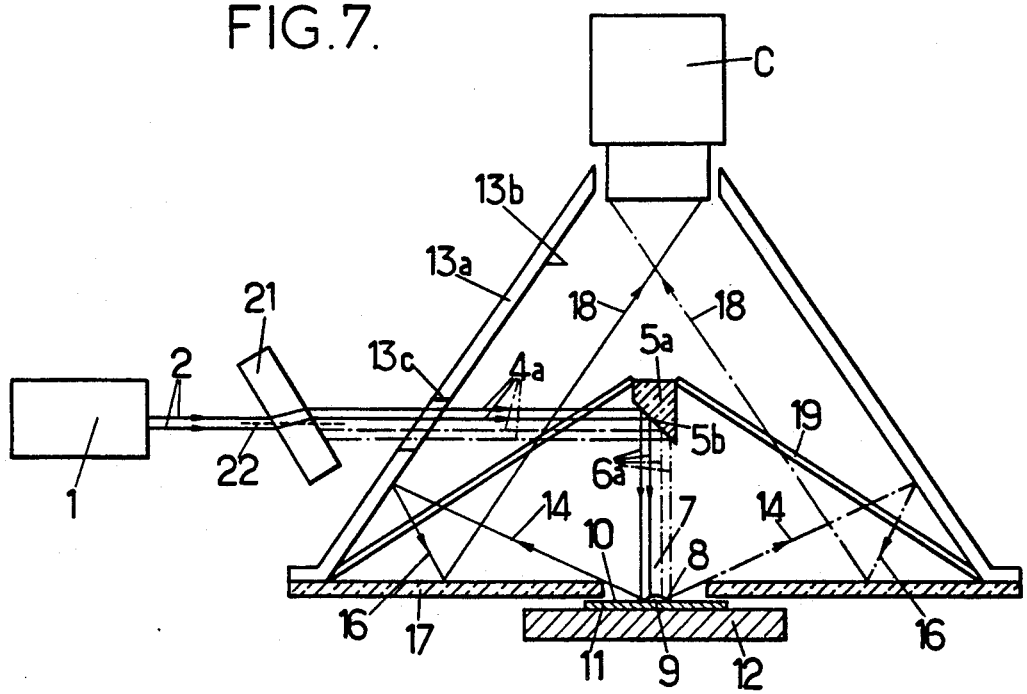

FIG. 7, finally, illustrates the application of the characteristic of FIG. 6 to a device of the invention, FIG. 7 being a variant of FIG. 3.

According to the invention and more particularly according to that one of its modes of application, as well as those of the embodiments of its different parts to which it seems preference should be given, wishing for example to improve the methods and devices for determining the contact angle of a drop of liquid placed on a substrate, the following or similar is the procedure to follow.

A first embodiment of a device according to the invention is illustrated in FIG. 3.

In FIG. 3, we find again a laser 1 emitting a beam 2 of horizontal and parallel rays which is widened, by an afocal optical system 3, into a more extensive beam 4 but also formed of horizontal and parallel rays.

A prism 5a, with a reflecting surface 5b slanted by 45° with respect to the vertical, reflects the horizontal beam 4 into a primary beam 6 of parallel light, vertical in direction, which illuminates a zone 7 including the interface between the periphery 8 of drop 9 and the horizontal surface 10 of substrate 11 carried movably by a support or sample holder 12.

According to a first characteristic of the invention, the rays 14 of the secondary beam from the interface between drop 9 and substrate 11, which form an angle equal to $2\theta'$ with the vertical, namely with rays 6, reach a receiving element 13 made from a reflection diffusing material with a reflecting face 13b. In particular, element 13a may be formed by an aluminium sheet or foil painted white on its face 13b.

Element 13a advantageously has a truncated cone shape, the angle at the apex of the cone corresponding to the angular field of camera C.

With this reflecting surface 13b, the rays 14 of the secondary beam are reflected as rays 16. The conical surface 13a is pierced with an orifice 13c for the passage of beam 4.

According to a second characteristic of the invention, a mirror 17 is provided forming a reflecting surface for rays 16 which are reflected as rays 18, a great part of which reach camera C, particularly when the angle at the apex of the cone formed by element 13a corresponds to the field of the camera, when the periphery of the small base of the truncated cone surrounds camera C and when the periphery of the large base thereof surrounds the reflecting surface formed by mirror 17.

It can be seen that, because of the structure of the device of FIG. 3 comprising the reflection diffusing surface 13b of the conical element 13a, on the one hand, and mirror 17 on the other, camera C receives a large part of the secondary beam of rays 14 after two reflections.

So that the rays 4 and 18 may pass without difficulty, the reflecting prism 5a is carried by a tripod 19.

Figure 4:
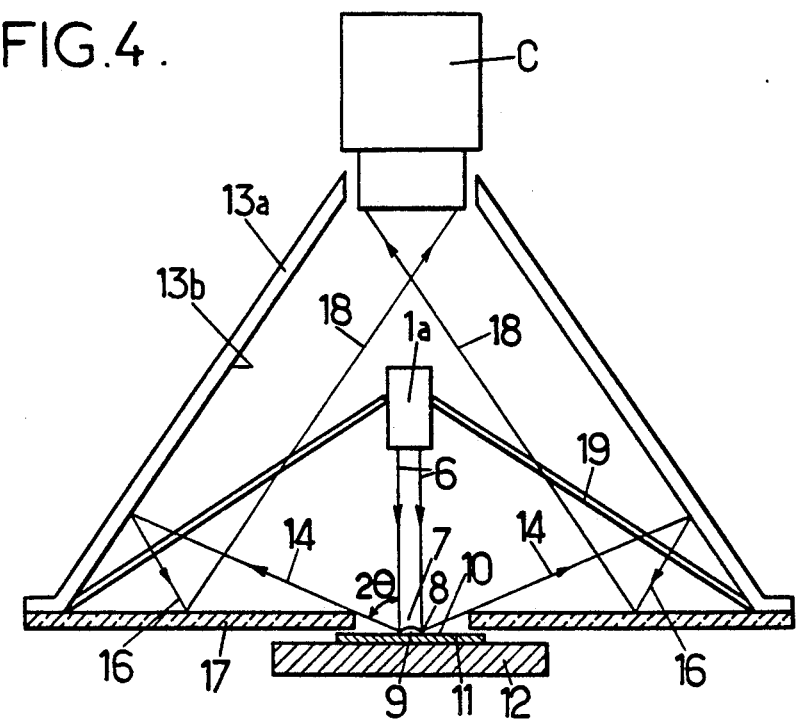
FIG. 4 is a variant of the embodiment of FIG. 3.

Instead of the assembly formed by laser 1, the afocal optical system 3 and the reflecting prism 5a of FIG. 3, in a variant illustrated in FIG. 4, a laser diode 1a may be simply provided (with collimation means not shown) of a small diameter, fixed directly to the tripod 19 formed by three metal rods. In this case, the diffusing conical element 13a does not need to be pierced.

Apart from these modifications, the embodiment of FIG. 4 is identical to that of FIG. 3 and the same reference numbers have been used, from reference 6, in FIG. 4 and in FIG. 3.

In the embodiment of FIG. 4, as in that of FIG. 3, camera C receives, as rays 18, a large part of the rays 14 of the secondary beam after reflection from the reflecting surface 13b of element 13a and from mirror 17.

Another problem which arises in the use of the method and device according to the French patent 2 574 180 mentioned above comes from the diffusion which occurs on the upper horizontal surface 10 of sample 11 when the latter is very diffusing, the extent of the illumination transition presented by the secondary beam in correspondence with the periphery of the drop being then very difficult to observe.

Figure 5:
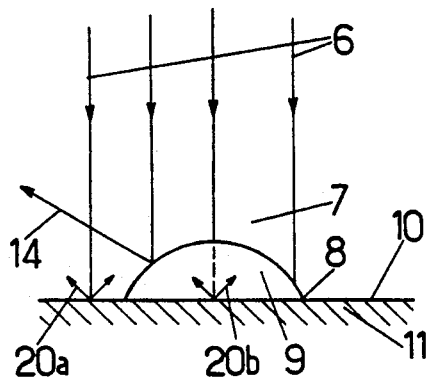
FIG. 5 shows the problems arising from the use of a device according to the above French patent and FIGS. 3 and 4 of the present application when the substrate is made from a diffusing material.

This phenomenon is illustrated in FIG. 5 in which has been shown the primary beam 6 of parallel and vertical rays which reach zone 7 including the periphery 8 of drop 9 and the flat upper horizontal surface 10 of substrate 11. In this figure, a ray 14 of the secondary beam has also been shown.

The phenomenon of diffusion at the surface 10 of substrate 11 is illustrated by parasite rays 20a and 20b resulting from the reflection of rays 6 of the primary beam from surface 10, not only rays 6 striking this surface 10 directly but also rays 6 passing through drop 9, whence respectively the parasite rays 20a and 20b.

According to a complementary characteristic of the invention, this drawback which occurs when the substrate is very diffusing is overcome by illuminating the periphery 8 of drop 9 by an annular beam, which limits the parasite diffusion.

This is illustrated in FIG. 6 in which the annular primary beam is illustrated by the endmost rays 6a which arrive at the level of periphery 8 of drop 9 placed on surface 10 of substrate 11. We find again a ray 14 of the secondary beam.

On the other hand, diffused rays of type 20a and 20b of FIG. 5 have not been shown since they are practically inexistent in the case of FIG. 6 when an annular primary beam 6a is used.

In FIG. 7, one embodiment of the invention has been illustrated comprising not only the improvements of FIG. 3, but also the arrangement of FIG. 6.

Figure 1:
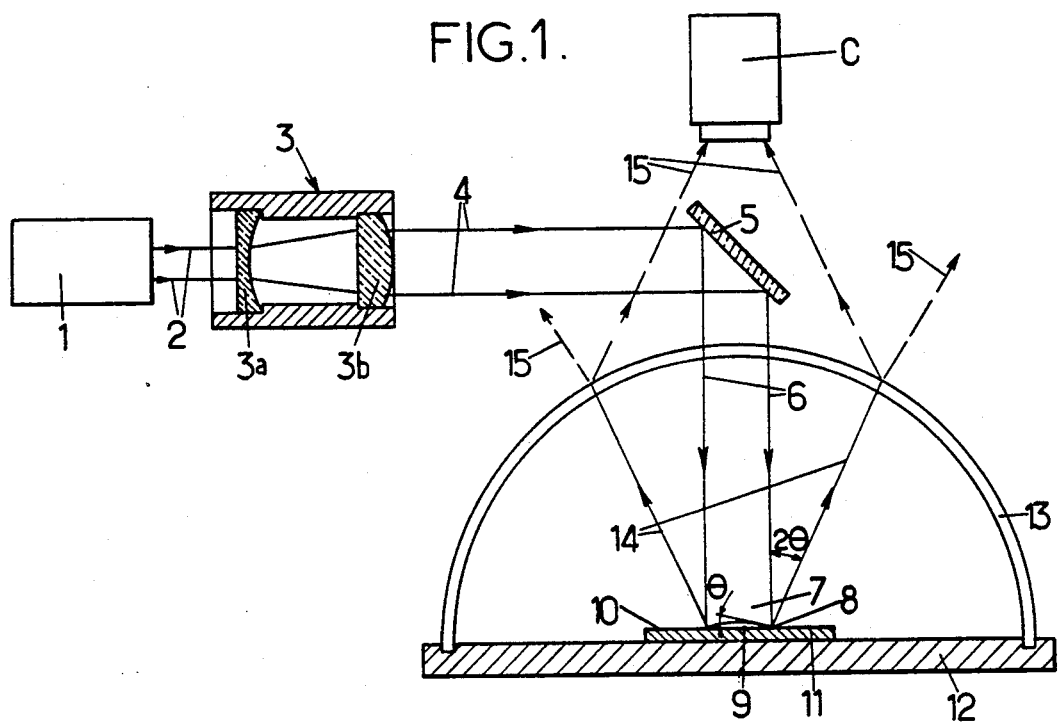
Figure 2:
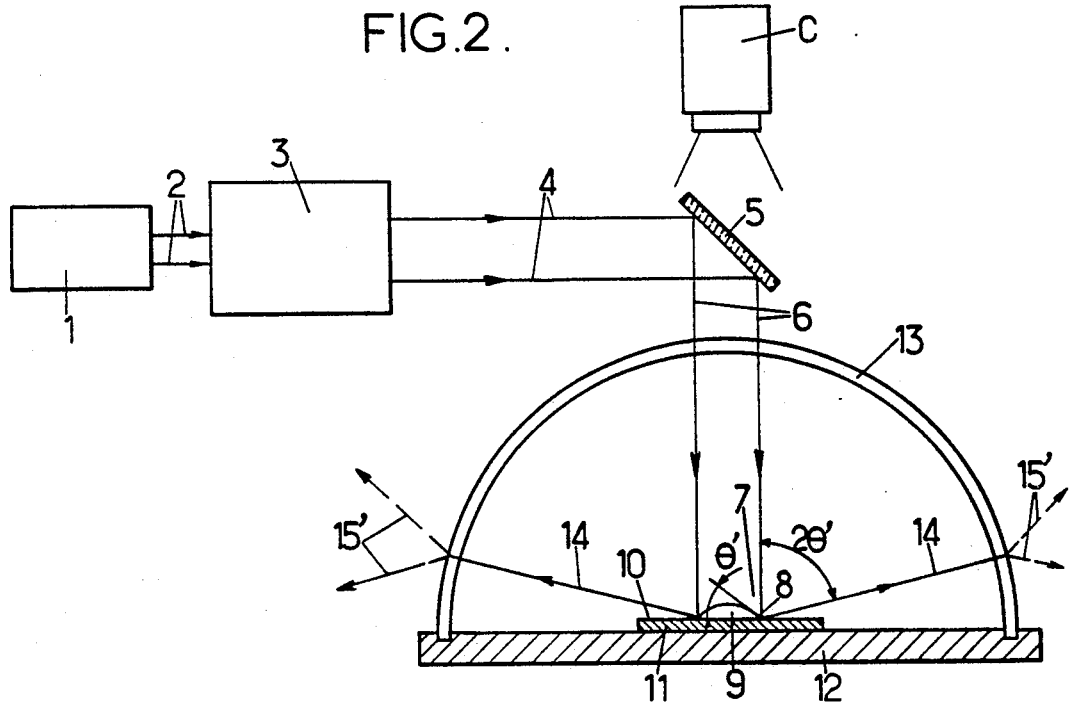

In this embodiment, a laser 1 emits a beam 2 of horizontal and parallel rays of coherent light, as in the embodiments of FIGS. 1, 2 and 3.

On the other hand, the device of FIG. 7 does not have an afocal optical system (of the type bearing the reference 3 in FIGS. 1, 2 and 3), but a thick plate 21 with parallel faces which is rotated (by means not shown) about its axis of rotation 22 while being slanted with respect to this axis. During rotation about axis 22 plate 21 produces, from beam 2, an annular beam 4a (in FIG. 7 the rays existing effectively at a given moment have been shown with continuous lines and with broken lines the rays generated at another time during rotation of plate 3a).

The mean ray of the annular beam 4a is given by the formula $$R = e \cdot \cos r \cdot (n-1)/n$$

r being the angle of inclination of the plate, e the thickness thereof and n the index of the glass forming the plate which may for example be equal to 1.5. By modifying the inclination of plate 21 with respect to its axis of rotation 22, it is therefore possible to adjust R so as to adapt it to the size of the liquid drop 9.

The annular beam 4a which has a horizontal axis, after passing through the opening 13c formed in the conical element 13a, is reflected by the surface 5b of a prism 5a, slanted by 45° with respect to the vertical, so as to form a primary annular beam 6a with vertical axis which strikes the contact zone of drop 9 and substrate 11, FIG. 6 in fact illustrating on a larger scale the portion of FIG. 7 in which the rays 6a arrive at the periphery of drop 9.

As in the embodiment of FIG. 3, rays 6a are reflected as rays 14 then sent back by the reflecting surface 13b as rays 16, and finally by mirror 17 as rays 18 which are collected by camera C.

It is clear that with the embodiment of FIG. 7, a universal device is obtained for determining the contact angle of a drop of liquid placed on a horizontal substrate, which is solid or liquid, because it gives satisfactory results, even for a high contact angle close to 45°, and even with a diffusing substrate, because camera C receives a large part of the rays such as 18 from the assembly of useful rays 14 of the secondary beam, even for a high contact angle, but receives practically no parasite rays (of type 20a, 20b of FIG. 5) which might be produced by diffusion when the substrate is very diffusing.

As is evident, the invention is in no wise limited to the modes of application and embodiments which have been more especially envisaged; it embraces, on the contrary, all variants thereof.

We claim:

1. Method for determining the contact angle of a drop of liquid placed on a substrate, for any contact angle less that 45°, which comprises the steps of:

directing perpendicularly to the substrate a primary beam of parallel light for illuminating a zone which contains an interface between the periphery of the drop and the substrate, determining the illumination transition zone presented onto at least one receiving surface by a secondary beam resulting from the interaction of the primary beam with the drop and the substrate, said receiving surface being a reflection diffusing surface, intercepting said secondary beam thereby forming a diffusing receiving surface emitting light rays, reflecting the light rays from said diffusing receiving surface through a reflecting surface disposed facing said diffusing receiving surface, and collecting the rays, reflected by said reflecting surface, by a camera.

2. Method according to claim 1, wherein the primary beam is annular.

3. Device for determining the contact angle of a drop of liquid placed on a substrate, for any contact angle less than 45°, in which a primary beam of parallel light is directed perpendicularly to the substrate for illuminating a zone which contains the interface between the periphery of the drop and the substrate, said device comprising:

at least one receiving surface, formed by a reflection diffusing surface, intercepting a secondary beam resulting from the interaction of said primary beam with the drop and the substrate, said at least one receiving surface forming a diffusing receiving surface emitting light rays, so as to determine the illumination transition zone presented onto said at least one receiving surface by said secondary beam, a reflecting surface disposed facing said diffusing receiving surface so as to reflect said light rays, and a camera for collecting said light rays reflected by said reflecting surface.

4. Device according to claim 3, wherein the diffusing receiving surface has the form of a hollow truncated cone whose small base periphery surrounds the camera and whose large base periphery surrounds said reflecting surface, the angle at the apex of the cone corresponding to the angular field of the camera.

5. Device according to claim 3 further comprising means for transforming the light beam emitted by the light source into an annular beam which will become the primary beam, also annular.

6. Device according to claim 5, characterized in that said means for transforming said light beam emitted by the light source into an annular beam comprises a plate with parallel faces whose inclination with respect to an axis of rotation may be modified, this axis being parallel to the direction of the rays of the light beam which the plate with parallel faces receives from the light source, and means for rotating the plate with parallel faces abut its axis of rotation.

7. Device according to claim 3, wherein the diffusing receiving surface is made from aluminum painted white.

* * * * *